United States Patent
Mercado et al.

(10) Patent No.: US 9,549,602 B2
(45) Date of Patent: Jan. 24, 2017

(54) FOUNDATION MAKEUP AND CONCEALER COMPOSITION

(71) Applicant: ELC Management LLC, Melville, NY (US)

(72) Inventors: Clara G. Mercado, Saddle River, NJ (US); John F. Logalbo, Dix Hills, NY (US); Aya Shidara, Douglaston, NY (US); Linda Carol McKenna, North Babylon, NY (US); Palmer McGuinness, Hartsdale, NY (US); Janet Pardo, New York, NY (US); Thomas Edward Owen, Montauk, NY (US)

(73) Assignee: ELC Management LLC, Melville, NY (US)

( * ) Notice: Subject to any disclaimer, the term of this patent is extended or adjusted under 35 U.S.C. 154(b) by 0 days.

(21) Appl. No.: 14/510,229

(22) Filed: Oct. 9, 2014

(65) Prior Publication Data

US 2016/0100669 A1    Apr. 14, 2016

(51) Int. Cl.
| | |
|---|---|
| A45D 33/00 | (2006.01) |
| A45D 34/04 | (2006.01) |
| A61K 8/29 | (2006.01) |
| A61K 8/891 | (2006.01) |
| A61Q 1/12 | (2006.01) |
| B65D 1/02 | (2006.01) |
| A61K 8/31 | (2006.01) |
| A61K 8/894 | (2006.01) |
| A45D 40/26 | (2006.01) |

(52) U.S. Cl.
CPC ............ *A45D 34/04* (2013.01); *A45D 40/267* (2013.01); *A61K 8/29* (2013.01); *A61K 8/31* (2013.01); *A61K 8/891* (2013.01); *A61K 8/894* (2013.01); *A61Q 1/12* (2013.01); *B65D 1/0207* (2013.01); *A61K 2800/43* (2013.01); *A61K 2800/594* (2013.01); *A61K 2800/87* (2013.01)

(58) Field of Classification Search
CPC ...... A45D 34/00; A45D 34/04; A45D 34/046; A45D 34/047; A45D 40/0068; A45D 40/26; A45D 40/262; A45D 40/265; A45D 40/267; A45D 40/28; A45D 2033/001
See application file for complete search history.

(56) References Cited

U.S. PATENT DOCUMENTS

| | | |
|---|---|---|
| 3,439,088 A | 4/1969 | Edman |
| 3,818,105 A | 6/1974 | Coopersmith et al. |
| 5,143,722 A | 9/1992 | Hollenberg et al. |

(Continued)

OTHER PUBLICATIONS

PCT International Search Report; International Application No. PCT/US2015/051843; Completion Date: Nov. 30, 2015; Mailing Date: Jan. 5, 2016.

(Continued)

*Primary Examiner* — Rachel Steitz
(74) *Attorney, Agent, or Firm* — Julie Blackburn

(57) ABSTRACT

A unitary packaged color cosmetic composition having a foundation makeup benefit and a concealer benefit, said composition stored in a receptacle having a closure and applicator, wherein the applicator has a foundation makeup benefit application section and a concealer benefit application section and the section of the applicator used to apply the composition to the keratin surface application area corresponds to the desired benefit.

7 Claims, 5 Drawing Sheets

(56) References Cited

U.S. PATENT DOCUMENTS

| | | | |
|---|---|---|---|
| 5,236,986 A | 8/1993 | Sakuta | |
| 5,412,004 A | 5/1995 | Tachibana et al. | |
| 5,800,816 A | 9/1998 | Brieva et al. | |
| 5,811,487 A | 9/1998 | Schulz, Jr. et al. | |
| 5,837,793 A | 11/1998 | Harashima et al. | |
| 6,331,085 B1 * | 12/2001 | Schrepf | A45D 34/046 401/122 |
| 6,622,733 B2 | 9/2003 | Saksa | |
| 7,607,850 B2 | 10/2009 | Weckerle et al. | |
| 8,312,696 B2 | 11/2012 | Dais et al. | |
| 8,662,776 B2 | 3/2014 | Porter et al. | |
| 2012/0093566 A1 * | 4/2012 | Gueret | A45D 34/046 401/122 |
| 2012/0204899 A1 * | 8/2012 | Uehara | A45D 34/045 132/320 |
| 2012/0282008 A1 | 11/2012 | Geuther et al. | |
| 2014/0037360 A1 | 3/2014 | Hofmann | |

OTHER PUBLICATIONS

PCT Written Opinion of the International Searching Authority; International Application No. PCT/US2015/051843; Completion Date: Nov. 30, 2015; Mailing Date: Jan. 5, 2016.

\* cited by examiner

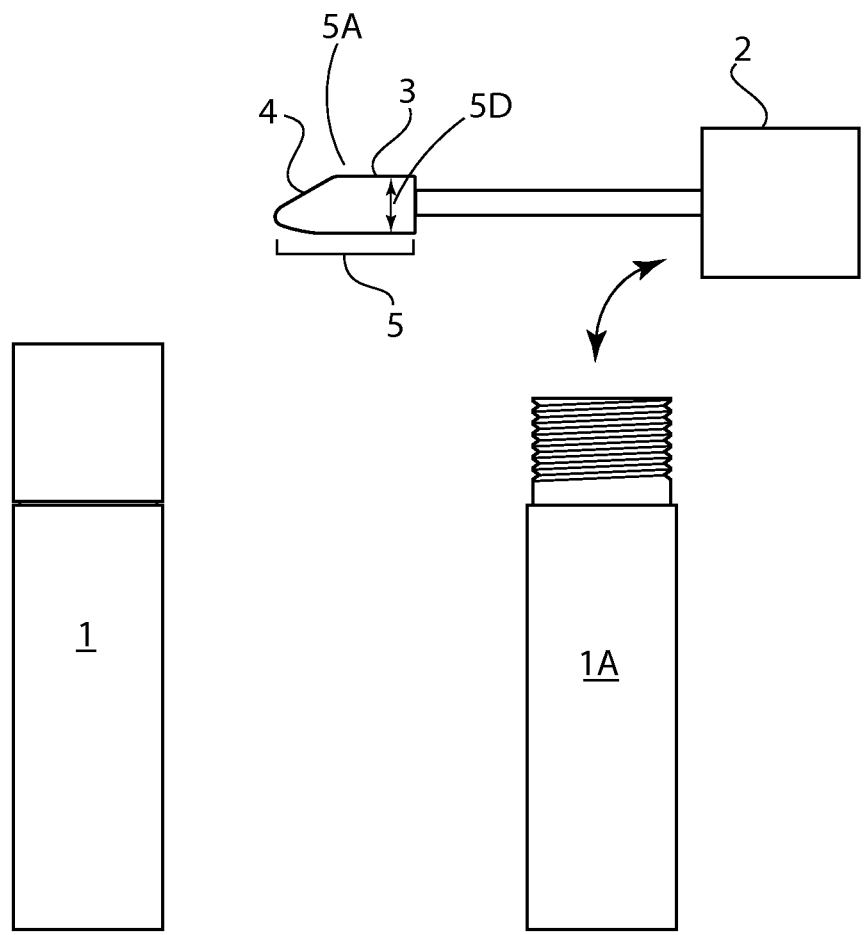
FIG. 1A
FIG. 1B
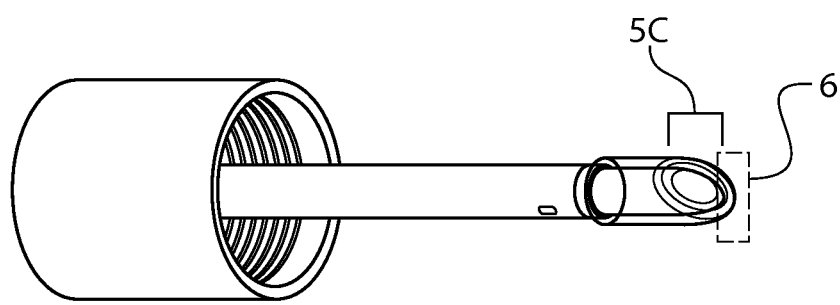
FIG. 2

FOUNDATION MAKEUP AND CONCEALER COMPOSITION

TECHNICAL FIELD

The invention is in the field of color cosmetic compositions for application to facial or body skin, and more specifically compositions that serve as a facial foundation makeup and under or around the eye concealer in one.

BACKGROUND OF THE INVENTION

Women are always interested in simplifying their beauty routines and minimizing the number of products they need to achieve the final desired result. Makeup products that are specifically designed for applying beneath or around the eyes to conceal superficial lines and wrinkles and undesirable coloration are quite popular. These products are called concealers and are most often sold in small tubes or containers with an applicator. They are applied in tiny dabs to the areas where concealment or correction is desired. What makes concealers effective is their ability to conceal flaws which in turn requires that the concealer have more coverage and opacity than color cosmetics that are not designed to conceal flaws. Most concealers tend to be viscous, have a significant amount of titanium dioxide or fillers to create opacity, and most often contain polymers that improve adhesion of the colored composition to the skin.

On the other hand, foundation makeup is meant to apply a colored film to skin that provides color correction and smoothness. Foundation makeup tends to be lighter in texture and has less opacity then concealer. As many users of both foundation and concealer know, they are not interchangeable. Attempts to use concealer on the entire face often result in finishes that are overly made up, rigid, subject to cracking, and with a tendency to feeling mask like and uncomfortable on the skin. Using standard foundation makeup under and around the eye area often results in minimal or no coverage at all, and sometimes causes smudging of eye makeup and mascara, leaving the user with the well known problem of raccoon eyes.

Accordingly, there is a need for a multi-benefit, multi-functional composition that colors the facial skin and eye area, provides adequate coverage, and optimal aesthetics and coverage as both a foundation and concealer. This multi-benefit product must also be easy to apply, and subject to storage and application from a container that is user friendly for consumers.

SUMMARY OF THE INVENTION

The invention is directed to a unitary packaged color cosmetic composition having a foundation makeup benefit and a concealer benefit, said composition stored in a receptacle having a closure and applicator, wherein the applicator has a foundation makeup benefit application section and a concealer benefit application section and the section of the applicator used to apply the composition to the keratin surface application area corresponds to the desired benefit.

The invention is also directed to a method for applying a color cosmetic composition having a foundation makeup benefit and a concealer benefit to a keratin surface application area with an applicator having sections for applying the composition to the keratin surface application area to achieve the desired benefit, comprising the steps of:

applying the composition to the keratin surface application area for which the concealer benefit is desired using the concealer benefit applicator section; and
applying the composition to the keratin surface application area for which the foundation makeup benefit is desired using the foundation makeup benefit applicator section.

The invention is also directed to water in oil multi-benefit foundation and concealer composition in one comprising, by weight of the total composition:
2-50% water,
1-30% titanium dioxide
0.1-1% of emulsifying crosslinked silicone elastomer,
1-15% dimethicone; and
1-20% of a volatile oil,
with the composition having a stabilized viscosity ranging from about 35,000 to 150,000, preferably from about 40,000 to 125,000, most preferably from about 40,000 to 110,000 centipoise at 25° C.

DETAILED DESCRIPTION

I. Definitions

Percentages mentioned herein shall mean percentage by weight unless otherwise indicated.

"Benefit" means the benefit that the cosmetic composition provides. A benefit may refer to the end use, e.g. foundation, concealer, etc.

"Keratin surface application area" means a section of a keratin surface to which the composition is applied to achieve the desired benefit.

"Plurality" means more than one.

"Semi-solid" means a composition that exists in a cream or paste and which is neither pourable nor solid at room temperature.

"Solid" means a composition that is a solid at room temperature (e.g. 25° C.).

"Stabilized viscosity" means that the viscosity of the composition stabilizes within 24 hours after manufacture and remains within a range of 35,000 to 150,000, most preferably from about 40,000 to 110,000 centipoise at 25° C.

"Unitary" means that it is a single composition that provides the desired benefits.

"Volatile" means that the ingredient has a vapor pressure of about 2 mm. of mercury or greater at 20° C.

II. DESCRIPTION OF THE DRAWINGS

FIG. 1(A): depicts the packaged composition of the invention stored in a closed package.

FIG. 1(B): depicts the packaged composition of the invention with the cap/applicator disengaged from the container.

FIG. 2 shows a perspective view of the cap/applicator used in the packaged composition.

III. THE PACKAGED COMPOSITION

Figure 3:
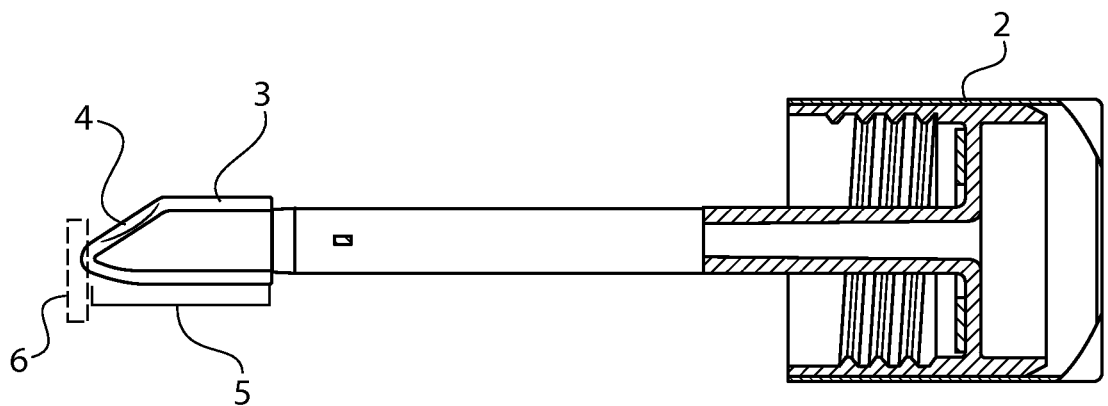
FIG. 3 is a side view of the cap/applicator used in the packaged composition.
Figure 4:
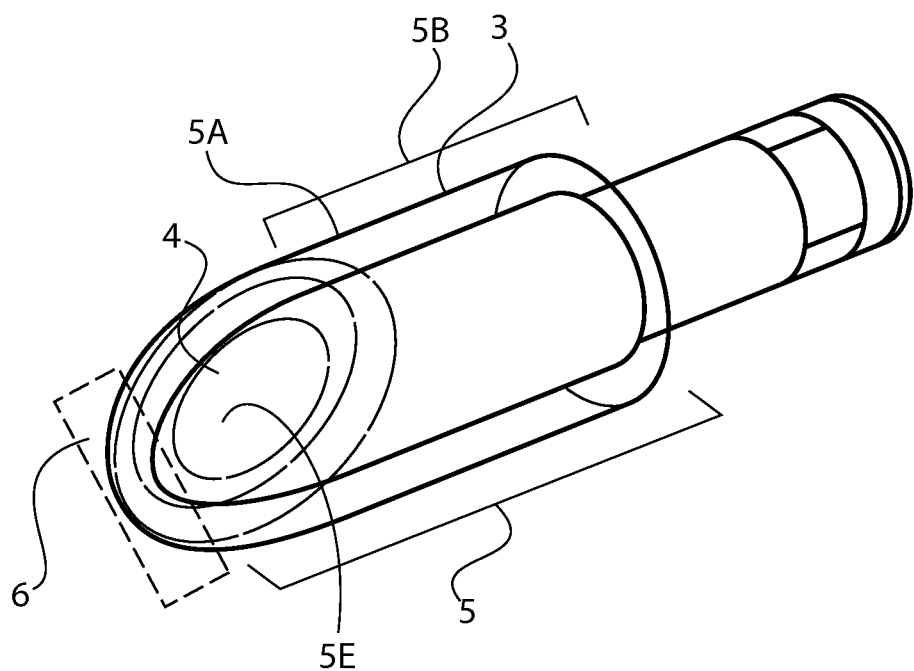
FIG. 4 is a magnified view of the applicator used in the packaged composition showing the sections used for application of the benefit composition to the desired keratin surface application areas.

The packaged composition of the invention 1 is a unitary packaged color cosmetic composition having a foundation makeup benefit and a concealer benefit. The composition is stored in a receptacle 1A having a closure 2 and applicator 3. The receptacle may be plastic or glass, but is preferably glass. The applicator has a foundation makeup benefit application section which is comprised of subsections 4, 5 and 5A as best seen in FIGS. 1B and 4. The applicator has a concealer benefit application section 6, best seen in FIGS. 2 and 4. The section of the applicator used to apply the composition to the keratin surface application area corresponds to the desired benefit.

Figure 5:
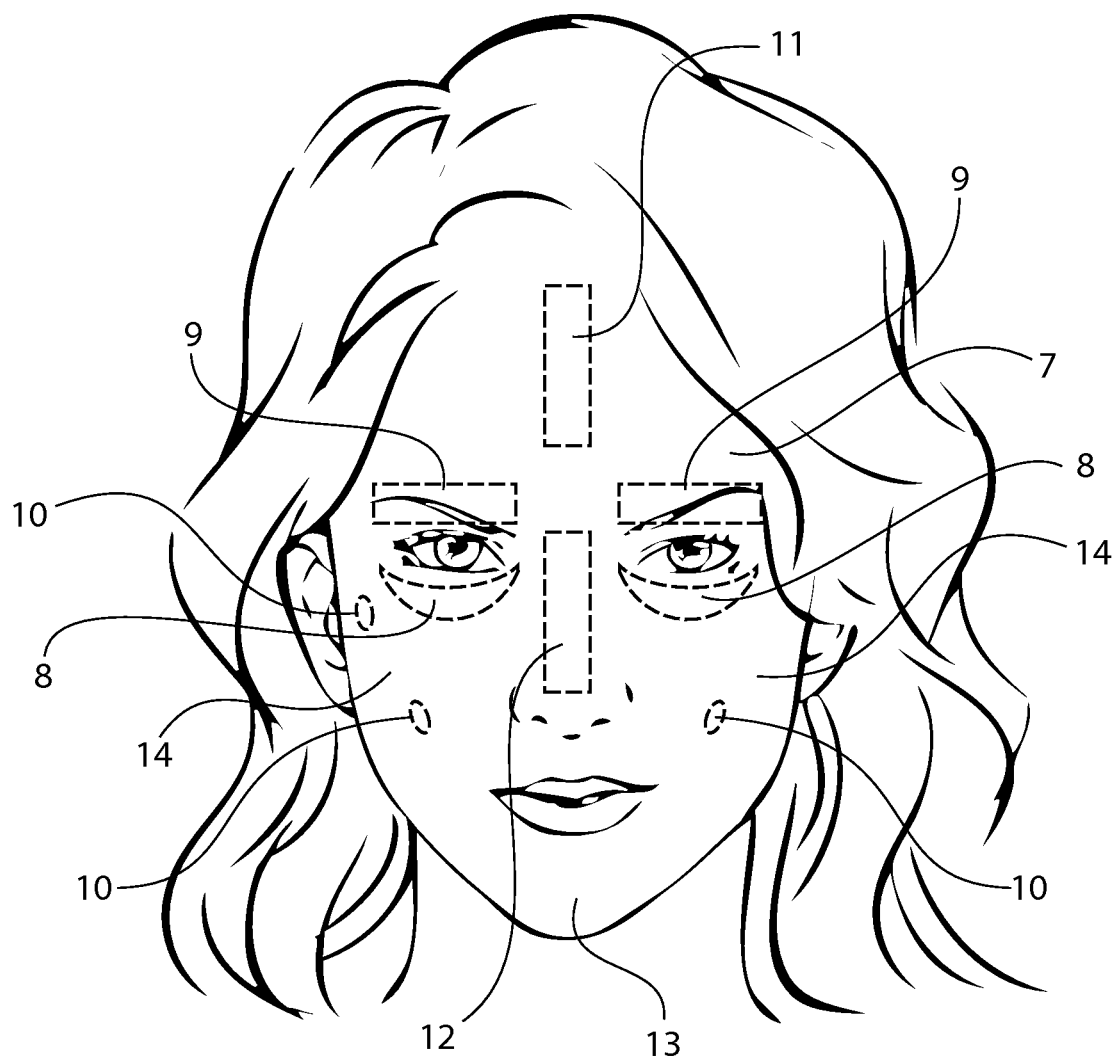
FIG. 5 depicts a keratin surface application area that is the face.

The concealer benefit is typically applied to discrete areas of a keratin surface application area such as a face 7 as best depicted in FIG. 5. The concealer benefit is typically applied to a keratin surface application area that is under the eye 8. The concealer benefit may also be applied to keratin surface application area that is the upper eyelid 9. The concealer benefit may be applied to the keratin surface application areas 8, 9 for which the concealer benefit is desired using corresponding concealer benefit subsection 6 of the applicator 3. Optionally, the concealer benefit may be applied to discrete areas of the face 7, for example to cover blemishes, scars, and the like, 10, in FIG. 5 as indicated by way of example.

Figure 7:
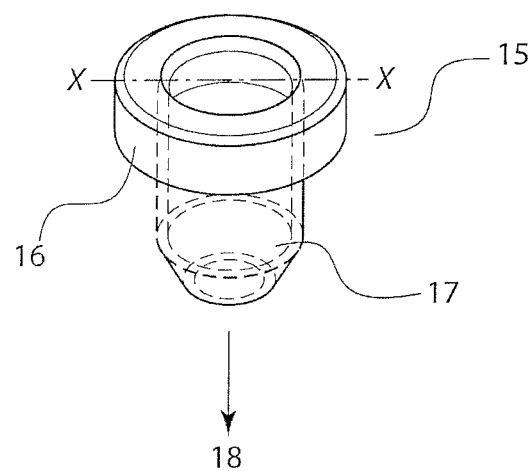
FIG. 7 depicts the wiper that is used in the container of the invention, specifically located in the neck of the container.

The foundation makeup benefit is typically applied to other discrete areas of the keratin surface application face area 7. The foundation makeup benefit is typically applied to forehead 11, nose 12, and chin 13, and remaining facial areas. The applicator 3 has sections that correspond to, and are for use in applying the composition to keratin surface application areas 11, 12, and 13. More specifically, the foundation makeup benefit applied to the forehead 11 and bridge of nose 12 and chin 13 is applied with section 4 of the applicator. The angled surface, preferably about 40-60°, preferably 45° provides a surface area preferably ranging from about 0.1 to 1.0, preferably from 0.2 to 0.7 square inches. More preferred is where the angled surface is concave 5E which permits a reservoir for holding the color cosmetic product. Preferred is where the overall length on the applicator 3 as shown in 5 (from the angled tip to the end of the flocked applicator) ranges from about 0.5 to 1.5, preferably from about 0.6 to 0.8 inches, most specifically 0.75 inch. Preferably the length as noted by section 5B of applicator (from the end of the angled tip closest to the rod to the end of the applicator) ranges from about 0.3 to 0.8, preferably from about 0.4 to 0.7, most preferred 0.54 inches and length of section 5C from about 0.1 to 0.4, preferably from about 0.2 to 0.3, more preferably from 0.274 inch. In one preferred embodiment of the invention, the width of the applicator 3 across its widest point 5C ranges from about 0.2 to 0.4 inch, preferably from about 0.22 to 0.32 inch. The applicator of the invention is preferably able to load about 0.1 to 1.2, preferably from about 0.2 to 1.0 grams of composition which is a sufficient amount for application to the entire face. Preferably the application load to all of the keratin surface application areas, in particular, the face, is done with one load of the composition where the different sections of the applicator are used to apply the cosmetic to the desired benefit areas. When the applicator is inserted into the composition and extracted, most preferred is where the load ranges from 0.1 to 1.0 grams. In order to provide an applicator that is operable to load a sufficient amount of the composition to color the whole face, the wiper used in the container must be capable of remaining affixed in its proper position within the neck of the container and withstanding a force of at least 9-13 pounds, preferably 10-12 pounds when the applicator is extracted from the container and through the wiper. This amount of force is needed to ensure adherence of the wiper in the neck of the glass container, and the force required in extracting the applicator from the container and through the wiper is necessary to ensure the desired load of 0.1 to 1.0 grams of composition onto the wiper—an amount sufficient to color the entire face. The preferred wiper 15 is set forth in FIG. 7, which is made from a thermoplastic material More specifically, the wiper 15 is comprised of a neck 16 which fits snugly into the neck of the receptacle 1A so that it remains firmly affixed in place when the applicator is extracted from the container through the wiper 15 with an amount of force ranging from 9-13, preferably 10-12 pounds. The wiper 15 contains a barrel portion 17 which is sufficient in volume to house the applicator 3. At the terminus of the barrel portion 17 of wiper 15 is an aperture 18 which is smaller in diameter and circumference then the diameter and circumference of the applicator 3. Preferably aperture 18 has a cross-sectional diameter ranging from 0.3 to 0.5, more preferably from about 0.35 to 0.45 inch. Applicator 3, when extracted from the container through wiper aperture 18 is capable of compressing to fit through aperture 18, and in so doing leaves an amount of product on the applicator that ranges from 0.1 to 1.0 grams of the composition to the keratin surface treatment area, which is sufficient for application to the entire face. Preferred is where the applicator is made of compressible sponge or flock that is capable of compressing when extracted through aperture 18 of wiper 15, and then expanding to its normal size after passing through aperture 18 of wiper 15.

Figure 8:
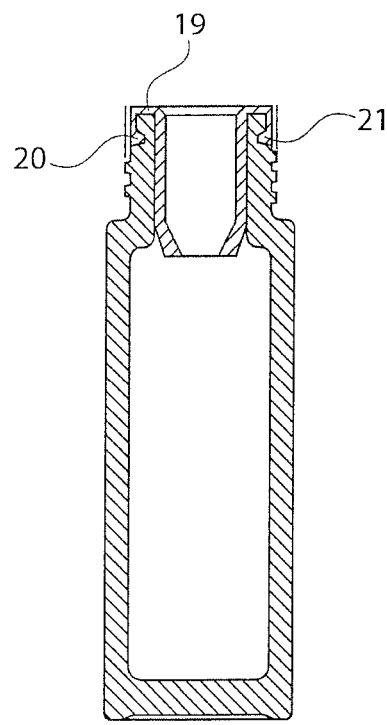
FIG. 8 is a cross sectional view of the wiper of FIG. 7 taken across X-X when seated into the receptacle 1A that contains the cosmetic product.

FIG. 8 depicts a cross sectional view of the wiper 15 seated in receptacle 1A. More specifically, the wiper shows extending arms 19 that curve downwardly in an approximate 90 degree angle and terminate in a club shaped circumferential protrusion 20 that mates with a corresponding circumferential cut away 21 in the neck of the receptacle 1A, which is preferably glass. Seating of wiper 15 in the neck of receptacle 1A enables wiper 15 to be secured in the neck of receptacle 1A and yet withstand a force of 9-13, preferably 10-12 pounds when the applicator is extracted from the receptacle 1A and used to apply the product to the keratin surface. The appropriate securing of the wiper 15 in the receptacle 1A, along with the configuration of the applicator, are all essential in causing the application to be loaded with an amount of product sufficient to make up the desired keratin surface to achieve the desired benefits.

The foundation makeup benefit applied to keratin surface application area 14, cheeks, may be applied with applicator sections 5 or 5A which have correspondingly larger surface areas to apply the composition to the larger keratinous surface application cheek 14 area.

Figure 6:
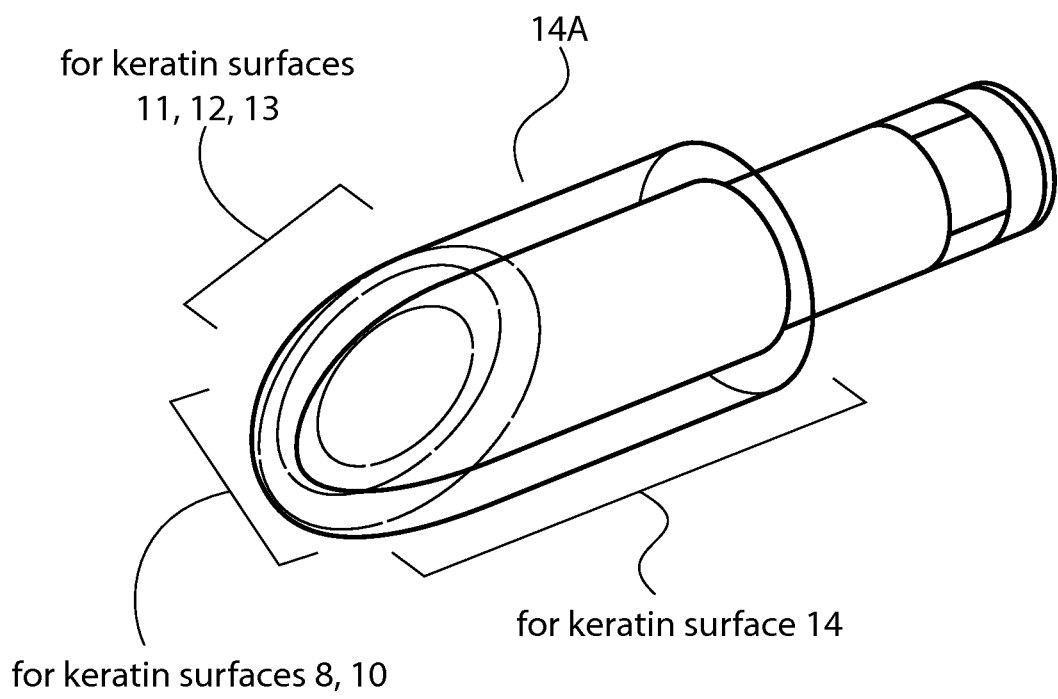
FIG. 6 shows the applicator of FIG. 4 where the sections of the applicator are numbered to correspond with the keratin surface application areas for which the applicator section is suggested for use.

FIG. 6 depicts the applicator of FIG. 4 where the applicator 3 is divided into sections and the sections are numbered to correspond to the keratin surface application area suggested for use in applying the composition to the desired keratin surface. For example numbered 8, 10 is a applicator section that is suggested for use with a concealer benefit, and in particular, for application to areas 8 and 10 depicted in FIG. 5. The square section of the applicator is marked with numbers 11, 12, and 13 to indicate that this section of the applicator is suggested for use in applying the composition to achieve a foundation makeup benefit, and preferably to forehead 11, bridge of nose 12, and chin 13. The large section of the applicator marked 14 in FIG. 6 indicates that this section of the applicator is suggested for use in creating a foundation makeup benefit and in particular for application to cheeks 14 and remaining facial surface which is larger and requires a larger amount of the composition to provide coverage. Section 14A may also be used to apply the composition to larger keratin surface application areas.

IV. The Method

The invention is also directed to a method for applying a color cosmetic composition having a foundation makeup benefit and a concealer benefit to a keratin surface application area with an applicator having separate and distinct sections for applying the composition to the keratin surface application area to achieve the desired benefit, comprising the steps of:
applying the composition to the keratin surface application area for which the concealer benefit is desired using the concealer benefit applicator section; and
applying the composition to the keratin surface application area for which the foundation makeup benefit is desired using the foundation makeup benefit applicator section.

Preferred is where the keratin surface application area for the concealer benefit is under the eye, above the eye, or on discrete areas on the facial surface where concealment of blemishes, flaws, or other skin irregularities is desired.

Preferred is where the keratin surface application area for the foundation makeup benefit is the forehead 11, nose 12, or chin 13.

The applicator may have subsections within the concealer benefit section or the foundation makeup benefit section. For example, the different subsections of the foundation makeup benefit section of the applicator may have different application areas that apply more or less composition depending on the keratin surface application section. More preferred is where the foundation makeup benefit section of the application has two subsections, designed as 4, 5 and 5A in FIG. 4. The subsection designated 4 is suggested for use in applying the composition to achieve the foundation makeup benefit to the keratin surface application areas of forehead, nose and chin, 11, 12, and 13 respectively. The foundation makeup benefit section of the application designed as subsection 5 or optionally 5A is suggested for us in applying the composition to larger keratin surface application areas such as the cheeks or other facial areas.

The application section for use in applying the composition to achieve the concealer benefit is designated 6 in the figures. Subsection 6 provides a much smaller surface and a correspondingly lower load of the composition is applied; desired for application.

The big advantage of the packaged composition of the invention is that one load of the applicator is sufficient to provide enough composition to color the entire keratin surface application area when it is the face. Thus, the user is not required to insert the applicator into the container multiple times to load enough product to make up the face. Applying exactly the right amount of the composition gives the right amount of coverage.

V. The Composition

The invention is also directed to a multi-benefit composition, more specifically a composition containing a foundation makeup benefit and a concealer benefit. The composition is a water in oil foundation and concealer composition in one comprising, by weight of the total composition:
2-45% water,
1-30% titanium dioxide
0.1-1% of emulsifying crosslinked silicone elastomer,
1-15% dimethicone; and
1-20% of a volatile solvent, preferably a volatile paraffinic hydrocarbon;
with the composition having a stabilized viscosity ranging from about 100,000 to 150,000, more preferably about 120,000 centipoise at room temperature (25° C.)

A. Dimethicone

The dimethicone present may be volatile or non-volatile. Examples of linear volatile silicones are those having the general formula:

$$(CH_3)_3Si-O-[Si(CH_3)_2-O]_n-Si(CH_3)_3$$

where n=0, 1, 2, 3, 4, or 5, preferably 0, 1, 2, 3, or 4.

Also suitable are non-volatile silicones Nonvolatile silicone oils, both water soluble and water insoluble, are also suitable for use in the composition. Such silicones preferably have a viscosity ranging from about greater than 5 to 800,000 cst, preferably 20 to 200,000 cst at 25° C. For example, such nonvolatile silicones may have the following general formula:

$$A-\underset{R}{\overset{R}{\underset{|}{Si}}}-O-\left[\underset{R}{\overset{R}{\underset{|}{Si}}}-O\right]_x-\left[\underset{R'}{\overset{R}{\underset{|}{Si}}}-O\right]_y-\underset{R}{\overset{R}{\underset{|}{Si}}}-A$$

wherein R and R' are each independently $C_{1-30}$ straight or branched chain, saturated or unsaturated alkyl, phenyl or aryl, trialkylsiloxy, and x and y are each independently 1-1,000,000; with the proviso that there is at least one of either x or y, and A is alkyl siloxy endcap unit.

Preferred is where A is a methyl siloxy endcap unit; in particular trimethylsiloxy, and R and R' are each independently a $C_{1-30}$ straight or branched chain alkyl, phenyl, or trimethylsiloxy, more preferably a $C_{1-22}$ alkyl, phenyl, or trimethylsiloxy, most preferably methyl, phenyl, or trimethylsiloxy, and resulting silicone is dimethicone, phenyl dimethicone, diphenyl dimethicone, phenyl trimethicone, or trimethylsiloxyphenyl dimethicone. Other examples include alkyl dimethicones such as cetyl dimethicone, and the like wherein at least one R is a fatty alkyl ($C_{12}$, $C_{14}$, $C_{16}$, $C_{18}$, $C_{20}$, or $C_{22}$), and the other R is methyl, and A is a trimethylsiloxy endcap unit, provided such alkyl dimethicone is a pourable liquid at room temperature. Phenyl trimethicone can be purchased from Dow Corning Corporation under the tradename 556 Fluid. Trimethylsiloxyphenyl dimethicone can be purchased from Wacker-Chemie under the tradename PDM-1000. Cetyl dimethicone, also referred to as a liquid silicone wax, may be purchased from Dow Corning as Fluid 2502, or from DeGussa Care & Surface Specialties under the trade names Abil Wax 9801, or 9814.

B. The Emulsifying Cross-linked Siloxane Elastomer

The composition also comprises at least one emulsifying crosslinked siloxane elastomer. Typically these polyoxyalkylenated silicone elastomers are crosslinked organopolysiloxanes that may be obtained by a crosslinking addition reaction of diorganopolysiloxane comprising at least one hydrogen bonded to silicon and of a polyoxyalkylene comprising at least two ethylenically unsaturated groups. In at least one embodiment, the polyoxyalkylenated crosslinked organo-polysiloxanes are obtained by a crosslinking addition reaction of a diorganopolysiloxane comprising at least two hydrogens each bonded to a silicon, and a polyoxyalkylene comprising at least two ethylenically unsaturated groups, optionally in the presence of a platinum catalyst, as described, for example, in U.S. Pat. No. 5,236,986 and U.S. Pat. No. 5,412,004, U.S. Pat. No. 5,837,793 and U.S. Pat. No. 5,811,487, the contents of which are incorporated by reference. Polyoxyalkylenated silicone elastomers that may be used include those sold by Shin-Etsu Silicones under the names KSG-21, KSG-20, KSG-30, KSG-31, KSG-32, KSG-33; KSG-210 which is dimethicone/PEG-10/15 crosspolymer dispersed in dimethicone; KSG-310 which is PEG-15 lauryl dimethicone crosspolymer; KSG-320 which is PEG-15 lauryl dimethicone crosspolymer dispersed in isododecane; KSG-330 (the former dispersed in triethylhexanoin), KSG-340 which is a mixture of PEG-10 lauryl dimethicone crosspolymer and PEG-15 lauryl dimethicone crosspolymer.

Also suitable are polyglycerolated silicone elastomers like those disclosed in PCT/WO 2004/024798, which is hereby incorporated by reference in its entirety. Such elastomers include Shin-Etsu's KSG series, such as KSG-710 which is dimethicone/polyglycerin-3 crosspolymer dispersed in dimethicone; or lauryl dimethicone/polyglycerin-3 crosspolymer dispersed in a variety of solvent such as isododecane, dimethicone, triethylhexanoin, sold under the Shin-Etsu tradenames KSG-810, KSG-820, KSG-830, or KSG-840. Also suitable are silicones sold by Dow Corning under the tradenames 9010 and DC9011.

One preferred crosslinked silicone elastomer emulsifier is dimethicone/PEG-10/15 crosspolymer, which provides excellent aesthetics due to its elastomeric backbone, but also surfactancy properties.

C. The Volatile Paraffinic Hydrocarbon

The composition comprises at least one volatile straight or branched chain paraffinic hydrocarbon having 5, 6, 7, 8, 9, 10, 11, 12, 13, 14, 15, 16, 17, 18, 19, or 20 carbon atoms, more preferably 8 to 16 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated by reference. Such paraffinic hydrocarbons are available from EXXON under the ISOPARS trademark, and from the Permethyl Corporation. Suitable $C_{12}$ isoparaffins are manufactured by Permethyl Corporation under the tradename Permethyl 99A. Various $C_{16}$ isoparaffins commercially available, such as isohexadecane (having the tradename Permethyl®), are also suitable.

D. Titanium Dioxide and Pigments

The composition comprises from about 5-45% titanium dioxide. The titanium dioxide may be coated or uncoated, and have a particle size ranging from 0.05 to 150 microns, preferably from about 20-100 microns. Preferably the composition also contains pigments which may be organic or inorganic. Examples of pigments include iron oxides The organic pigments are generally various aromatic types including azo, indigoid, triphenylmethane, anthroquinone, and xanthine dyes which are designated as D&C and FD&C blues, browns, greens, oranges, reds, yellows, etc. Organic pigments generally consist of insoluble metallic salts of certified color additives, referred to as the Lakes. Inorganic pigments include iron oxides, ultramarines, chromium, chromium hydroxide colors, and mixtures thereof. Iron oxides of red, blue, yellow, brown, black, and mixtures thereof are suitable.

E. Other Ingredients

The composition may also contain other ingredients including but not limited to those set forth below.

1. Other Volatile Oils

Suitable volatile oils generally have a viscosity ranging from about 0.5 to 5 centistokes 25° C. and include linear or cyclic silicones, paraffinic hydrocarbons, or mixtures thereof.

(a). Cyclic Volatile Silicones

Cyclic silicones are one type of volatile silicone that may be used in the composition, including those having the following formula:

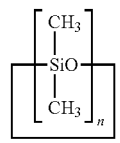

wherein=3-6, preferably 4, 5, or 6. Preferred is where n=5 or 6, with such silicones having the CTFA names cyclopentasiloxane or cyclohexasiloxane.

Cyclic silicones are available from various commercial sources including Dow Corning Corporation and General Electric. The Dow Corning linear volatile silicones are sold under the tradenames Dow Corning 244, 245, 344, and 200 fluids. These fluids include hexamethyldisiloxane (viscosity 0.65 centistokes (abbreviated cst)), octamethyltrisiloxane (1.0 cst), decamethyltetrasiloxane (1.5 cst), dodecamethylpentasiloxane (2 cst) and mixtures thereof, with all viscosity measurements being at 25° C.

Branched volatile silicones may also be present, including alkyl trimethicones such as methyl trimethicone, ethyl trimethicone, propyl trimethicone, butyl trimethicone and the like. Methyl trimethicone may be purchased from Shin-Etsu Silicones and has the trade name TMF 1.5, having the viscosity of 1.5 centistokes at 25° C. Such silicones have the general formula:

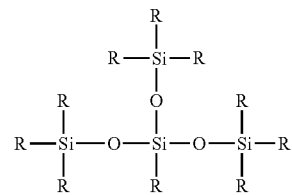

wherein each R is independently a $C_{1-4}$ alkyl, preferably methyl.

2. Other Non-Volatile Oils

A variety of nonvolatile oils are also suitable for use in the compositions of the invention. The nonvolatile oils generally have a viscosity of greater than about 5 to 10 centistokes at 25° C., and may range in viscosity up to about 1,000,000 centistokes at 25° C. Examples of nonvolatile oils include, but are not limited to:

(a). Esters

Suitable esters are mono-, di-, and triesters. The composition may comprise one or more esters selected from the group, or mixtures thereof.

Monoesters are defined as esters formed by the reaction of a monocarboxylic acid having the formula R—COOH, wherein R is a straight or branched chain saturated or unsaturated alkyl having 2 to 45 carbon atoms, or phenyl;

and an alcohol having the formula R—OH wherein R is a straight or branched chain saturated or unsaturated alkyl having 2-30 carbon atoms, or phenyl. Both the alcohol and the acid may be substituted with one or more hydroxyl groups. Either one or both of the acid or alcohol may be a "fatty" acid or alcohol, and may have from about 6 to 30 carbon atoms, more preferably 12, 14, 16, 18, or 22 carbon atoms in straight or branched chain, saturated or unsaturated form. Examples of monoester oils that may be used in the compositions of the invention include hexyl laurate, butyl isostearate, hexadecyl isostearate, cetyl palmitate, isostearyl neopentanoate, stearyl heptanoate, isostearyl isononanoate, steary lactate, stearyl octanoate, stearyl stearate, isononyl isononanoate, and so on.

Suitable diesters are the reaction product of a dicarboxylic acid and an aliphatic or aromatic alcohol, or an aliphatic or aromatic alcohol having at least two substituted hydroxyl groups and a monocarboxylic acid. The dicarboxylic acid may contain from 2 to 30 carbon atoms, and may be in the straight or branched chain, saturated or unsaturated form. The dicarboxylic acid may be substituted with one or more hydroxyl groups. The aliphatic or aromatic alcohol may also contain 2 to 30 carbon atoms, and may be in the straight or branched chain, saturated, or unsaturated form. Preferably, one or more of the acid or alcohol is a fatty acid or alcohol, i.e. contains 12-22 carbon atoms. The dicarboxylic acid may also be an alpha hydroxy acid. The ester may also be in the dimer or trimer form. Examples of diester oils that may be used in the compositions of the invention include those having a lower viscosity, e.g. diisostearyl malate, neopentyl glycol dioctanoate, dibutyl sebacate, dicetearyl dimer dilinoleate, dicetyl adipate, diisocetyl adipate, diisononyl adipate, diisostearyl dimer dilinoleate, diisostearyl fumarate, diisostearyl malate, dioctyl malate, and so on.

Suitable triesters comprise the reaction product of a tricarboxylic acid and an aliphatic or aromatic alcohol, or alternatively, the reaction product of an aliphatic or aromatic alcohol having three or more substituted hydroxyl groups with a monocarboxylic acid. As with the mono- and diesters mentioned above, the acid and alcohol contain 2 to 30 carbon atoms, and may be saturated or unsaturated, straight or branched chain, and may be substituted with one or more hydroxyl groups. Preferably, one or more of the acid or alcohol is a fatty acid or alcohol containing 12 to 22 carbon atoms. Examples of triesters include esters of arachidonic, citric, or behenic acids, such as triarachidin, tributyl citrate, triisostearyl citrate, tri $C_{12-13}$ alkyl citrate, tricaprylin, tricaprylyl citrate, tridecyl behenate, trioctyldodecyl citrate, tridecyl behenate; or tridecyl cocoate, tridecyl isononanoate, and so on.

Esters suitable for use in the composition are further described in the C.T.F.A. Cosmetic Ingredient Dictionary and Handbook, Eleventh Edition, 2006, under the classification of "Esters", the text of which is hereby incorporated by reference in its entirety.

(b). Hydrocarbon Oils

It may be desirable to incorporate one or more nonvolatile hydrocarbon oils into the composition. Suitable nonvolatile hydrocarbon oils include paraffinic hydrocarbons and olefins, preferably those having greater than about 20 carbon atoms. Examples of such hydrocarbon oils include $C_{24-28}$ olefins, $C_{30-45}$ olefins, $C_{20-40}$ isoparaffins, hydrogenated polyisobutene, polyisobutene, polydecene, hydrogenated polydecene, mineral oil, pentahydrosqualene, squalene, squalane, and mixtures thereof. In one preferred embodiment such hydrocarbons have a molecular weight ranging from about 300 to 1000 Daltons.

(c). Glyceryl Esters of Fatty Acids

Synthetic or naturally occurring glyceryl esters of fatty acids, or triglycerides, are also suitable for use in the compositions. Both vegetable and animal sources may be used. Examples of such oils include castor oil, lanolin oil, $C_{10-18}$ triglycerides, caprylic/capric/triglycerides, sweet almond oil, apricot kernel oil, sesame oil, camelina sativa oil, tamanu seed oil, coconut oil, corn oil, cottonseed oil, linseed oil, ink oil, olive oil, palm oil, illipe butter, rapeseed oil, soybean oil, grapeseed oil, sunflower seed oil, walnut oil, and the like.

Also suitable are synthetic or semi-synthetic glyceryl esters, such as fatty acid mono-, di-, and triglycerides which are natural fats or oils that have been modified, for example, mono-, di- or triesters of polyols such as glycerin. In an example, a fatty ($C_{12-22}$) carboxylic acid is reacted with one or more repeating glyceryl groups. glyceryl stearate, diglyceryl diiosostearate, polyglyceryl-3 isostearate, polyglyceryl-4 isostearate, polyglyceryl-6 ricinoleate, glyceryl dioleate, glyceryl diisotearate, glyceryl tetraisostearate, glyceryl trioctanoate, diglyceryl distearate, glyceryl linoleate, glyceryl myristate, glyceryl isostearate, PEG castor oils, PEG glyceryl oleates, PEG glyceryl stearates, PEG glyceryl tallowates, and so on.

3. Humectants

The compositions of the invention may also contain one or more humectants. If present, suggested ranges are from about 0.001 to 50%, preferably from about 0.01 to 45%, more preferably from about 0.05 to 40% by weight of the total composition. Examples of suitable humectants include glycols, sugars, and the like. Suitable glycols are in monomeric or polymeric form and include polyethylene and polypropylene glycols such as PEG 4-200, which are polyethylene glycols having from 4 to 200 repeating ethylene oxide units; as well as $C_{1-6}$ alkylene glycols such as propylene glycol, butylene glycol, pentylene glycol, and the like. Suitable sugars, some of which are also polyhydric alcohols, are also suitable humectants. Examples of such sugars include glucose, fructose, honey, hydrogenated honey, inositol, maltose, mannitol, maltitol, sorbitol, sucrose, xylitol, xylose, trehalose, and so on. Also suitable is urea or sugar derivatives, e.g. ethylhexylglycerin. In one preferred embodiment, the humectants used in the composition of the invention are $C_{1-6}$, preferably $C_{2-4}$ alkylene glycols, most particularly butylene glycol.

4. Surfactants

If desired, the compositions of the invention may contain one or more surfactants in addition to the emulsified cross-linked siloxane elastomer. If present, the surfactant may range from about 0.001 to 50%, preferably from about 0.005 to 40%, more preferably from about 0.01 to 35% by weight of the total composition. Suitable surfactants may be silicone or organic, nonionic, anionic, amphoteric or zwitterionic. Such surfactants include, but are not limited to, those set forth herein.

(a). Silicone Surfactants

Suitable silicone surfactants include linear polyorganosiloxane polymers that have amphiphilic properties, for example contain hydrophilic radicals and lipophilic radicals. These silicone surfactants may be liquids or solids at room temperature.

One type of silicone surfactant that may be used is generically referred to as dimethicone copolyol or alkyl dimethicone copolyol. It may be either a water-in-oil or oil-in-water surfactant having an Hydrophile/Lipophile Balance (HLB) ranging from about 2 to 18. Preferably the silicone surfactant is a nonionic surfactant having an HLB ranging from about 2 to 12, preferably about 2 to 10, most preferably about 4 to 6. The term "hydrophilic radical" means a radical that, when substituted onto the organosiloxane polymer backbone, confers hydrophilic properties to the substituted portion of the polymer. Examples of radicals that will confer hydrophilicity are hydroxy-polyethyleneoxy, hydroxyl, carboxylates, and mixtures thereof. The term "lipophilic radical" means an organic radical that, when substituted onto the organosiloxane polymer backbone, confers lipophilic properties to the substituted portion of the polymer. Examples of organic radicals that will confer lipophilicity are $C_{1-40}$ straight or branched chain alkyl, fluoro, aryl, aryloxy, $C_{1-40}$ hydrocarbyl acyl, hydroxy-polypropyleneoxy, or mixtures thereof.

One type of suitable silicone surfactant has the general formula:

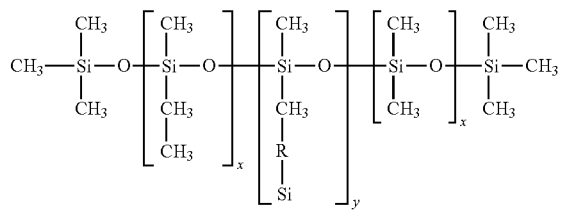

wherein p is 0-40 (the range including all numbers between and subranges such as 2, 3, 4, 13, 14, 15, 16, 17, 18, etc.), and PE is $(-C_2H_4O)_a-(-C_3H_6O)_b-H$ wherein a is 0 to 25, b is 0-25 with the proviso that both a and b cannot be 0 simultaneously, x and y are each independently ranging from 0 to 1 million with the proviso that they both cannot be 0 simultaneously. In one preferred embodiment, x, y, z, a, and b are such that the molecular weight of the polymer ranges from about 5,000 to about 500,000, more preferably from about 10,000 to 100,000, and is most preferably approximately about 50,000 and the polymer is generically referred to as dimethicone copolyol.

One type of silicone surfactant is wherein p is such that the long chain alkyl is cetyl or lauryl, and the surfactant is called, generically, cetyl dimethicone copolyol or lauryl dimethicone copolyol respectively.

In some cases the number of repeating ethylene oxide or propylene oxide units in the polymer are also specified, such as a dimethicone copolyol that is also referred to as PEG-15/PPG-10 dimethicone, which refers to a dimethicone having substituents containing 15 ethylene glycol units and 10 propylene glycol units on the siloxane backbone. It is also possible for one or more of the methyl groups in the above general structure to be substituted with a longer chain alkyl (e.g. ethyl, propyl, butyl, etc.) or an ether such as methyl ether, ethyl ether, propyl ether, butyl ether, and the like.

Examples of silicone surfactants are those sold by Dow Corning under the tradename 5225C Formulation Aid, having the CTFA name cyclopentasiloxane (and) PEG/PPG-18/18 dimethicone; or Dow Coming 190 Surfactant having the CTFA name PEG/PPG-18/18 dimethicone; or Dow Corning 193 Fluid, Dow Corning 5200 having the CTFA name lauryl PEG/PPG-18/18 methicone; or Abil EM 90 having the CTFA name cetyl PEG/PPG-14/14 dimethicone sold by Goldschmidt; or Abil EM 97 having the CTFA name bis-cetyl PEG/PPG-14/14 dimethicone sold by Goldschmidt; or Abil WE 09 having the CTFA name cetyl PEG/PPG-10/1 dimethicone in a mixture also containing polyglyceryl-4 isostearate and hexyl laurate; or KF-6011 sold by Shin-Etsu Silicones having the CTFA name PEG-11 methyl ether dimethicone; KF-6012 sold by Shin-Etsu Silicones having the CTFA name PEG/PPG-20/22 butyl ether dimethicone; or KF-6013 sold by Shin-Etsu Silicones having the CTFA name PEG-9 dimethicone; or KF-6015 sold by Shin-Etsu Silicones having the CTFA name PEG-3 dimethicone; or KF-6016 sold by Shin-Etsu Silicones having the CTFA name PEG-9 methyl ether dimethicone; or KF-6017 sold by Shin-Etsu Silicones having the CTFA name PEG-10 dimethicone; or KF-6038 sold by Shin-Etsu Silicones having the CTFA name lauryl PEG-9 polydimethylsiloxyethyl dimethicone.

(b). Organic Nonionic Surfactants

The composition may comprise one or more nonionic organic surfactants. Suitable nonionic surfactants include alkoxylated alcohols, or ethers, formed by the reaction of an alcohol with an alkylene oxide, usually ethylene or propylene oxide. Preferably the alcohol is either a fatty alcohol having 6 to 30 carbon atoms. Examples of such ingredients include Steareth 2-100, which is formed by the reaction of stearyl alcohol and ethylene oxide and the number of ethylene oxide units ranges from 2 to 100; Beheneth 5-30 which is formed by the reaction of behenyl alcohol and ethylene oxide where the number of repeating ethylene oxide units is 5 to 30; Ceteareth 2-100, formed by the reaction of a mixture of cetyl and stearyl alcohol with ethylene oxide, where the number of repeating ethylene oxide units in the molecule is 2 to 100; Ceteth 1-45 which is formed by the reaction of cetyl alcohol and ethylene oxide, and the number of repeating ethylene oxide units is 1 to 45, Laureth 2-100, formed by the reaction of lauryl alcohol and ethylene oxide where the number of repeating ethylene oxide units is 2 to 100, and so on.

Other alkoxylated alcohols are formed by the reaction of fatty acids and mono-, di- or polyhydric alcohols with an alkylene oxide. For example, the reaction products of $C_{6-30}$ fatty carboxylic acids and polyhydric alcohols which are monosaccharides such as glucose, galactose, methyl glucose, and the like, with an alkoxylated alcohol. Examples include polymeric alkylene glycols reacted with glyceryl fatty acid esters such as PEG glyceryl oleates, PEG glyceryl stearate; or PEG polyhydroxyalkanotes such as PEG dipolyhydroxystearate wherein the number of repeating ethylene glycol units ranges from 3 to 1000. Also suitable are ethoxylated propoxylated derivatives of C6-30 saturated or unsaturated fatty acids, for example, Di-PPG-2 myreth-10 adipate, Di-PPG-2 Ceteth-4 adipate, Di-PPG Myristyl Ether Adipate, Other nonionic surfactants that may be used are formed by the reaction of a carboxylic acid with an alkylene oxide or with a polymeric ether or monomeric, homopolymeric, or block copolymeric ethers; or alkoxylated sorbitan and alkoxylated sorbitan derivatives. For example, alkoxylation, in particular ethoxylation of sorbitan provides polyalkoxylated sorbitan derivatives. Esterification of polyalkoxylated sorbitan provides sorbitan esters such as the polysorbates. For example, the polyalkyoxylated sorbitan can be esterified with C6-30, preferably C12-22 fatty acids. Examples of such ingredients include Polysorbates 20-85, sorbitan oleate, sorbitan sesquioleate, sorbitan palmitate, sorbitan sesquiisostearate, sorbitan stearate, and so on.

5. Film Formers

It may be desired to incorporate one or more film formers into the compositions of the invention. Film formers will generally enhance the film formed by the cosmetic applied to the skin and, in some cases, promote water resistance or transfer resistance. If present, such film formers may range from about 0.1 to 50%, preferably from about 0.5 to 40%, more preferably from about 1 to 35% by weight of the total composition.

Suitable film formers may be based on silicone or organic polymers. Particularly preferred are crosslinked silicone resins generally referred to as MT or MQ resins. Examples of such resins include the MQ resin trimethylsiloxysilicate or an MT resin called polymethylsilsesquioxane. Trimethylsiloxysilicate may be purchased from Dow Corning under the tradename 749 Fluid which is about a 50/50 mixture of trimethylsiloxysilicate and cyclomethicone, or General Electric under the tradename SR1000. Polymethylsilsesquioxane may be purchased from Wacker-Chemie under the tradename MK resin.

The composition may contain other ingredients including preservatives, botanical extracts, vitamins, antioxidants, and the like.

The invention will be described in connection with the following examples which are set forth for purposes of illustration only.

Example 1

A makeup and concealer composition in one was made as follows:

| Ingredient | % by weight |
| --- | --- |
| Deionized water | QS100 |
| Titanium dioxide | 22.0 |
| Isostearyl neopentanoate | 17.0 |
| Dimethicone | 7.26 |
| Isohexadecane | 6.10 |
| Trimethylsiloxysilicate | 4.00 |
| Butylene glycol | 3.00 |
| Mica | 3.00 |
| Iron oxides | 2.80 |
| Glycerin | 2.00 |
| Lauryl PEG-9 Polydimethylsiloxy dimethicone | 2.00 |
| Trehalose | 1.00 |
| HDI/Trimethylolhexyllactone crosspolymer | 1.00 |
| Dimethicone/PEG-10/15 crosspolymer | 0.70 |
| Triethoxycaprylylsilane | 0.60 |
| Bismuth oxychloride | 0.50 |
| Sodium chloride | 0.50 |
| Tocopheryl acetate | 0.50 |
| Zinc oxide | 0.50 |
| PMMA | 0.50 |
| Propylene carbonate | 0.21 |
| Lecithin | 0.20 |
| Laureth-7 | 0.15 |
| Silica | 0.12 |
| Disodium EDTA | 0.10 |
| Hydrogenated lecithin | 0.10 |
| Magnesium aluminum silicate | 0.10 |
| Dimethicone silylate | 0.08 |
| Xanthan gum | 0.05 |
| Dipropylene glycol | 0.02 |
| Sodium hyaluronate | 0.01 |

The composition was prepared by combining the water phase and oil phase ingredients and mixing well to emulsify. The resulting composition was a water in oil emulsion having a viscosity ranging from about 454,000 cps at room temperature initially, with viscosity increasing and stabilizing to about 120,000 cps and maintaining from 24 hours to 20 weeks.

Example 2

The composition of Example 1 was tested on panelists for various desired attributes. More specifically, the Example 1 composition was tested for wear on 11 panelists with fair skin. The composition was applied to the skin by a trained cosmetologist. After 12 hours the amount of color retention remaining on the skin was measured. For the Example 1 composition, 82% of the composition remained on the skin after 12 hours of wear.

Example 3

The composition of Example 1 was applied to the volar forearm of 11 panelists in a 2 cm.×2 cm. square. After the composition dried on the skin it was rinsed with water. After the first, second, and third washes, 98%, 96%, and 93%, respectively, of the composition remained on the skin. Thus, the composition of Example 1 exhibited excellent skin adherence even after multiple rinses with water with 98% of the composition remaining on skin after rinse #1, 96% of the composition remaining on the skin after rinse #2, and 93% of the composition remaining on the skin after rinse #3.

Example 4

The composition of Example 1 was applied to the facial skin of 11 panelists by a trained cosmetologist. Immediately after the composition dried on the skin, and then at 2, 4, 6, and 8 hours the amount of sebum on the skin was clinically assessed by a trained clinician. The Example 1 composition reduced skin surface sebum by an average of 11%. More specifically, the sebum reduction at 2, 4, and 6 hours was 20%, 15%, and 11% respectively.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

We claim:

1. A unitary packaged color cosmetic composition having a foundation makeup benefit and a concealer benefit stored in a glass receptacle with a neck having a circumferential cutaway and having secured therein a wiper made of a thermoplastic material, a closure, and an applicator with compressible sponge or flock having a foundation makeup benefit application section having at least one subsection for applying the composition to small areas of the face and at least one subsection for applying the composition to large areas of the face to achieve the foundation makeup benefit, and a concealer benefit application section for applying the composition to discrete sections of the face to achieve the concealer benefit where the section of the applicator used to apply the composition to each area of the face corresponds to the desired benefit for that area of the face and wherein the wiper has: (i) a barrel portion that has sufficient volume to contain the applicator, (ii) an aperture smaller in diameter than the width of the applicator at the terminus of the barrel portion, (iii) a neck which is seated in the neck of the receptacle and has extending arms that curve downwardly to terminate in club shaped circumferential protrusions that mate with the circumferential cutaway in the neck of the receptacle such that the wiper is operable to withstand at least 9 to 13 pounds of pressure when the applicator is compressed as it is pulled through the aperture when extracted from the receptacle by the user to cause the load of the composition on the applicator to be an amount sufficient to make up the entire face to achieve the foundation makeup and concealer benefits.

2. The packaged composition of claim 1 wherein the wiper is operable to withstand a force of 10-12 pounds when the applicator is extracted from the receptacle by the user.

3. The packaged composition of claim 1 wherein the composition comprises, by weight of the total composition, 2-50% water, 1-30% titanium dioxide, 0.1-1% of an emulsifying crosslinked silicone elastomer, 1-15% dimethicone, 1-20% volatile oil and has a stabilized viscosity of 35,000 to 150,000 centipoise at 25° C.

4. The packaged composition of claim 3 wherein the one subsection of the foundation makeup benefit application section for applying the composition to small areas of the face has an application surface that is angled from 40 to 60 degrees having a concave surface forming a reservoir for holding cosmetic product.

5. The packaged composition of claim 4 wherein the application surface is angled at about 45° and has a surface area of about 0.2 to 0.7 inches.

6. The packaged composition of claim 1 wherein the extending arms of the wiper curve downwardly in an approximate 90 degree angle.

7. The packaged composition of claim 1 wherein the wiper is seated in the neck of the receptacle in a manner sufficient to withstand a force of at least 10 pounds when the applicator is extracted from the receptacle by the user.

* * * * *